(12) United States Patent
Ries et al.

(10) Patent No.: US 11,730,342 B2
(45) Date of Patent: Aug. 22, 2023

(54) DETECTION SYSTEM AND METHOD FOR AUTOMATIC DETECTION OF SURGICAL INSTRUMENTS

(71) Applicant: JOIMAX GMBH, Karlsruhe (DE)

(72) Inventors: Wolfgang Ries, Linkenheim (DE); Rainer Steegmüller, Gerlingen (DE); Maximilian Ries, Karlsruhe (DE)

(73) Assignee: JOIMAX GMBH, Karlsruhe (DE)

( * ) Notice: Subject to any disclaimer, the term of this patent is extended or adjusted under 35 U.S.C. 154(b) by 488 days.

(21) Appl. No.: 16/636,580

(22) PCT Filed: Aug. 24, 2018

(86) PCT No.: PCT/EP2018/000413
§ 371 (c)(1),
(2) Date: Feb. 4, 2020

(87) PCT Pub. No.: WO2019/042579
PCT Pub. Date: Mar. 7, 2019

(65) Prior Publication Data
US 2021/0153724 A1    May 27, 2021

(30) Foreign Application Priority Data
Aug. 29, 2017 (DE) .................... 10 2017 008 148.4

(51) Int. Cl.
*A61B 1/00* (2006.01)
*A61B 34/20* (2016.01)
(Continued)

(52) U.S. Cl.
CPC ...... *A61B 1/00087* (2013.01); *A61B 1/00064* (2013.01); *A61B 1/00097* (2022.02);
(Continued)

(58) Field of Classification Search
CPC ................ A61B 1/00158; A61B 5/062; A61B 2034/2051; A61B 1/00087;
(Continued)

(56) References Cited

U.S. PATENT DOCUMENTS 5,318,025 A * 6/1994 Dumoulin .............. A61B 5/055
600/417
5,325,873 A * 7/1994 Hirschi ............. A61M 25/0127
600/424

(Continued)

FOREIGN PATENT DOCUMENTS

| AU | 2013 251 245 B2 | 5/2015 |
| EP | 1 442 715 A2 | 8/2004 |
| JP | H08542 A | 1/1996 |

*Primary Examiner* — Ryan N Henderson
*Assistant Examiner* — Shankar Raj Ghimire
(74) *Attorney, Agent, or Firm* — McGlew and Tuttle, P.C.

(57) ABSTRACT

An automatic detection of surgical instruments with respect to a type and a location thereof is provided with a detection system, which includes at least two surgical instruments, which each include at least one cavity extending along a longitudinal axis of the instrument and a proximal entry region to the cavity. An angle of the proximal entry region in relation to the longitudinal extension of the cavity is different in the two instruments. A sensor unit includes two electromagnetic sensors and is insertable into the cavity. One of the sensors extends axially in the cavity, and the other sensor is arranged in the entry region. A field generator generates an electromagnetic field. An analysis unit analyzes signals transmitted by the sensors to the analysis unit in accordance with the location thereof in the field of the field generator.

20 Claims, 11 Drawing Sheets

(51) Int. Cl.
  *A61B 1/012* (2006.01)
  *A61B 1/313* (2006.01)
  *A61B 1/01* (2006.01)
  *A61B 5/06* (2006.01)

(52) U.S. Cl.
  CPC ...... *A61B 1/00121* (2013.01); *A61B 1/00124* (2013.01); *A61B 1/00128* (2013.01); *A61B 1/00135* (2013.01); *A61B 1/00158* (2013.01); *A61B 1/01* (2013.01); *A61B 1/012* (2013.01); *A61B 1/3135* (2013.01); *A61B 5/062* (2013.01); *A61B 34/20* (2016.02); *A61B 2034/2051* (2016.02)

(58) Field of Classification Search
  CPC ............ A61B 1/00097; A61B 1/00124; A61B 1/00128; A61B 1/012; A61B 1/3135; A61B 34/20
  See application file for complete search history.

(56) References Cited

U.S. PATENT DOCUMENTS

| | | | | |
|---|---|---|---|---|
| 5,735,793 | A * | 4/1998 | Takahashi | A61B 1/00128 600/153 |
| 6,059,718 | A * | 5/2000 | Taniguchi | A61B 5/06 600/117 |
| 6,511,417 | B1 * | 1/2003 | Taniguchi | A61B 5/06 600/117 |
| RE40,852 | E * | 7/2009 | Martinelli | A61B 5/062 128/899 |
| 7,706,859 | B2 * | 4/2010 | Aizawa | A61B 5/06 600/117 |
| 8,147,404 | B2 * | 4/2012 | Miyoshi | A61B 5/06 600/177 |
| 8,192,354 | B2 * | 6/2012 | Miyake | A61B 34/20 600/117 |
| 8,197,494 | B2 * | 6/2012 | Jaggi | A61B 5/06 606/130 |
| 8,211,010 | B2 * | 7/2012 | Hirakawa | A61B 34/20 600/117 |
| 8,257,247 | B2 * | 9/2012 | Oda | A61B 1/009 600/117 |
| 8,265,732 | B2 * | 9/2012 | Besz | A61B 5/743 600/407 |
| 8,611,984 | B2 * | 12/2013 | Greenburg | A61B 34/20 600/424 |
| 9,456,766 | B2 * | 10/2016 | Cox | A61M 25/0102 |
| 9,554,716 | B2 * | 1/2017 | Burnside | A61B 5/283 |
| 9,727,963 | B2 * | 8/2017 | Mintz | A61B 1/005 |
| 10,478,254 | B2 * | 11/2019 | Krimsky | A61B 10/04 |
| 11,000,207 | B2 * | 5/2021 | Burnside | A61B 5/6852 |
| 11,058,446 | B2 * | 7/2021 | Gliner | A61B 5/062 |
| 2004/0097805 | A1 | 5/2004 | Verard et al. | |
| 2004/0143158 | A1 * | 7/2004 | Hart | A61B 90/30 600/114 |
| 2004/0249287 | A1 * | 12/2004 | Kawashima | A61B 8/4488 600/462 |
| 2007/0164900 | A1 | 7/2007 | Schneider et al. | |
| 2009/0281419 | A1 * | 11/2009 | Troesken | A61B 90/36 342/450 |
| 2012/0101508 | A1 * | 4/2012 | Wook Choi | B25J 9/1697 700/259 |
| 2013/0267835 | A1 * | 10/2013 | Edwards | A61B 34/20 600/424 |
| 2014/0051993 | A1 | 2/2014 | McGee | |
| 2014/0155709 | A1 * | 6/2014 | Ikai | A61B 1/00158 600/302 |
| 2014/0180328 | A1 * | 6/2014 | Vaccaro | A61M 29/02 606/196 |
| 2014/0303437 | A1 * | 10/2014 | Kikuchi | A61B 1/00133 600/106 |
| 2016/0045334 | A1 * | 2/2016 | Ries | A61F 2/4611 623/17.16 |
| 2016/0278757 | A1 * | 9/2016 | Piskun | A61B 1/313 |
| 2017/0196535 | A1 * | 7/2017 | Arai | A61B 8/0841 |
| 2017/0215762 | A1 * | 8/2017 | Burnside | A61B 5/6852 |
| 2018/0193098 | A1 * | 7/2018 | Caluser | A61B 34/20 |
| 2018/0333044 | A1 * | 11/2018 | Jenkins | A61B 1/00128 |
| 2018/0368918 | A1 * | 12/2018 | Tatsui | A61B 34/20 |

\* cited by examiner

DETECTION SYSTEM AND METHOD FOR AUTOMATIC DETECTION OF SURGICAL INSTRUMENTS

CROSS REFERENCE TO RELATED APPLICATIONS

This application is a United States National Phase Application of International Application PCT/EP2018/000413, filed Aug. 24, 2018, and claims the benefit of priority under 35 U.S.C. § 119 of German Application 10 2017 008 148.4, filed Aug. 29, 2017, the entire contents of which are incorporated herein by reference.

TECHNICAL FIELD

The invention relates to an automatic detection system for automatic detection of surgical instruments, an intraoperative navigation device comprising such a system, a sensor unit for use in a detection system, and a method for automatic detection of surgical instruments.

TECHNICAL BACKGROUND

Minimally invasive operations are already carried out presently by means of navigation-assisted operating methods. Different navigation systems are used for this purpose. Active and passive systems are used. In active systems, a part introduced into the body of a patient, such as an instrument or surgical tool, is provided with a transmitter, via which the position of the instrument or tool, in particular the distal end located at the engagement location, may be externally determined.

In passive systems, in addition to optical systems for positioning a surgical instrument, in particular its distal end, electromagnetic systems are also known. In electromagnetic navigation, an inhomogeneous electromagnetic field is generated by a field generator, which is detected via one or more sensors, whereby the position and alignment of the instrument or surgical tool, in particular its distal end, can in turn be detected directly or indirectly. Direct detection of the distal end of a surgical part includes the arrangement of the sensor on the distal end of the part itself; indirect detection includes the fixed rigid attachment of the sensor in a defined point, in particular axial position, on the surgical part. Inferences about the position and possibly the orientation of the distal end can be seen on the basis of the measured sensor signal. In passive navigation, in particular electromagnetic navigation has proven itself, in which an electromagnetic field is generated externally around the operation region, for example, by a generator of an electromagnetic field in a cushion on which the patient lies. Coil-type sensors installed in the surgical instrument enable the locating of the instruments, whereupon a representation can be performed in CT or MRT images. This method does not include a radiation exposure and thus overall reduces the radiation exposure, also due to a reduced use of x-rays. The image quality is not impaired, nor can sensors be concealed, since they are not optical sensors. The freedom of movement of the operator is not restricted, as is the case with optical systems.

SUMMARY

The invention is based on an object of providing a detection system, a sensor unit, and a navigation system which effectuate automatic detection of the type of a surgical instrument and the position in the patient and also a correspondingly adapted display on a monitor for the operator.

The invention provides, with regard to the achievement of the mentioned object, a detection system having at least two surgical instruments, which each comprise at least one cavity extending along a longitudinal axis of the instrument and a proximal entry region to the cavity, wherein an angle of the proximal entry region in relation to the longitudinal extension of the cavity is different in the at least two instruments, having a sensor unit, which comprises two electromagnetic sensors and is insertable into the cavity, one sensor of which is arranged extending axially in the cavity and the other sensor of which is arranged in the entry region, having a field generator for generating an electromagnetic field, and having an analysis unit for analyzing signals transmitted to the analysis unit by the sensors in accordance with the location thereof in the field of the field generator. In the scope of the invention, a sensor unit is characterized by at least two of the following instruments: hollow needle, guide rod, penetration needle according to Jamshidi, and/or endoscope of such a detection system. Furthermore, the object is achieved by an intraoperative navigation system having a control and processing electronics unit and having at least one sensor unit of the above-mentioned type electrically connectable thereto, in which the control and processing electronics unit comprises a detection unit, a navigation unit, and a camera system. Finally, a method for automatic detection of surgical instruments is provided to achieve the mentioned object, in which the angle orientation of two sensors of a sensor unit arranged with fixed longitudinal spacing from one another is determined.

Typical operation instruments or devices are those, such as a rotationally-symmetrical hollow needle, a guide rod, a penetration needle, in particular according to Jamshidi, which are guided distally to the operation location, or also endoscopes having an angled inlet insert, such as a flushing port. The sensor unit according to the invention is also elongated upon arrangement in the first-mentioned elongated hollow needle, whereby the two sensors are arranged in axial succession and are oriented aligned, i.e., the angle between them is zero. In contrast, if the corresponding sensor unit is arranged in an endoscope, the distal sensor is located at the distal end of the solely axial shaft of the endoscope, while the proximal sensor is arranged in an inlet attachment of the endoscope and thus encloses a specific angle in relation to the axis of the shaft of the endoscope and therefore also in relation to the sensor provided at the distal end. A relative angle thus exists between the two sensors.

Other instruments, such as a guide rod, penetration needles, or the like can comprise the corresponding angled entry region having definable angled inlet of an endoscope and other angles differing from one another, whereby the angle orientation of the located sensors thereof is determined by a flexible sensor unit.

The above-mentioned differences of the relative orientation of the sensors can be detected by an analysis unit of an electronic system and therefore form the requirement for detection of the type of the surgical instrument or device in which the sensor unit is arranged. In this case, the position of the instrument is also determined via the sensors.

The detection and further processing of the detected information is performed by the mentioned analysis unit by this unit detecting the relative orientation of the two sensors and the position and controlling a display screen display on a monitor of an intraoperative operation system for the operator in such a way that the image or images suitable for the respective instrument or device are displayed.

An access to an operation region in the body of a patient is provided by means of a rotationally-symmetrical hollow needle, so that subsequently other operation instruments can be introduced in a way known per se. If such a needle is detected, through which suitable working instruments are optionally introduced, in addition to a respective sagittal, coronal, and axial CT, MRT, or x-ray image of the spinal column region, in particular of the spinal column and more precisely the location of the spinal column at which the operation region is located, an image corresponding to the guide direction of the hollow needle and thus of the working instrument to be used is automatically displayed together with this image by superposition in the correct location and orientation of the needle or needle tip, for example, by a circle significantly highlighted from the other representation of the image as a projection of the hollow needle tip on the operation location as an orientation aid for the correct positioning of the instrument.

In contrast, upon recognition of an endoscope as a surgical instrument or device, in addition to the mentioned sagittal, coronal, and axial x-ray images having superimposed overlay of the endoscope shaft accurately in location and orientation in the x-ray image, is additionally the image of the operation region recorded by a camera in the endoscope is automatically displayed on the monitor of the operator.

This applies correspondingly to further surgical instruments such as guide rods, penetration needles, or the like.

One preferred embodiment of the detection system according to the invention is characterized by at least two of the following instruments: hollow needle, guide rod, penetration needle according to Jamshidi, and/or endoscope, wherein preferably the guide rod is double cannulated. One preferred design of the detection system is characterized by at least four different instruments.

In one refinement, it is provided that the angles of the entry regions to the longitudinal extension of the cavity of two instruments differ by at least 5° from one another, wherein the entry regions of the instruments preferably have angles of 0°, 65°, or 35° in relation to the longitudinal extension of the cavity of the instrument.

One preferred refinement provides that the sensors have a fixed longitudinal spacing in relation to one another.

In one refinement, it is provided that the sensors are coils made of electrically conductive wire, wherein in particular the coils consist of metal, in particular copper or silver.

In preferred refinements, it can be provided in particular that the sensor unit comprises a flexible protective tubing jacketing the sensors, wherein in particular the protective tubing consists of plastic, in particular of biocompatible plastic which can be sterilized, such as polyether.

For the exact fixing of the sensor unit on the surgical instrument or device, an adapter, in particular a Luer adapter is provided, which, as known, typically consists of a female and a male adapter part. A sensor unit is preferably accordingly formed in that an adapter part is arranged proximal of the proximal sensor. It preferably consists of plastic, such as biocompatible plastic which can be sterilized, in particular nylon.

Further preferred embodiments provide an electrical connecting line of the sensors at the proximal end, in particular for the connection to the analysis unit, wherein in particular the electrical connecting line is enclosed by a protective tubing made of biocompatible plastic which can be sterilized, in particular silicone, and/or the protective tubing is enclosed directly proximal of the adapter part of the sensor unit by a buckling safeguard, wherein in addition in an extremely preferred embodiment, it is provided that the buckling safeguard is enclosed by biocompatible plastic which can be sterilized, in particular silicone.

In principle, it is preferably provided in this case that the analysis unit is part of a control and processing electronics unit, wherein furthermore a monitor can be provided. In an extremely preferred embodiment, the design is provided for the representation of at least two instruments, such as a hollow needle, a guide rod, which is double cannulated in particular, a penetration needle, and/or an endoscope, in particular of the distal end, of instruments overlaid in an image of a spinal column region of a patient.

An intraoperative navigation device according to the invention comprises a control and processing electronics unit and a detection system according to the invention, wherein the control and processing electronics unit itself comprises a navigation unit, in which the analysis unit is integrated.

A sensor unit according to the invention is one which comprises at least one or more features of the sensor unit of the above-described detection system.

One preferred refinement of the method according to the invention provides that upon detection of a specific relative angle orientation of the two sensors, an instrument corresponding to an angle orientation is recognized and a representation of the respective instrument, in particular the distal end, is effectuated overlaid in an image of a spinal column region of a patient, wherein the image is in particular a CT, MRT, or x-ray image.

An endoscope is controlled via the control unit of the camera system and provides an image to a processing unit of the camera system. This image is transmitted to the navigation system.

The navigation system consisting of various functional software components, the processing unit, the control unit, and the field generator is connected to the camera system and the sensor unit and also to the monitor for the display. The sensor unit can be used either for navigation of a rotationally-symmetrical instrument or an endoscope, in that this is inserted either into the shaft of the instrument or into the flushing channel of the endoscope.

The field generator generates an electromagnetic, inhomogeneous field and is controlled via the control unit of the navigation system. The signals of the sensor coils of the wire sensor are digitized via the processing unit and analyzed via the functional software components. The functional unit instrument recognition analyzes the signals of the two sensor coils and recognizes on the basis of the orientation of the two coils in relation to one another whether the sensor unit is located in an endoscope or not. The functional unit instrument recognition relays the result to the functional unit layout control. In dependence on whether the navigation software recognizes an endoscope or not, the corresponding layout is displayed on the monitor via the layout control. If the endoscope is recognized by the software, the video signal is fed via the functional unit into the navigation system and is provided to the functional unit for the layout output.

If an endoscope is not recognized via the corresponding functional unit on the basis of the accurately defined orientation of the two sensor coils in relation to one another, a rotationally-symmetrical instrument and the corresponding layout representation are output.

The sequence of the method according to the invention is preferably as follows:

After starting of the navigation unit, the signals of the sensors are requested. As soon as the user moves the sensor unit into the working field of the field generator, a signal can be recognized and measured. If the sensor signal is not equal to the value zero (sensor in the working field), instrument recognition takes place. For this purpose, the orientation of the two sensors for the sensor coils is analyzed. If the two sensors are oriented (distance and angle) in this case in relation to one another in accordance with the geometry of the flushing channel of an endoscope, i.e., having relative angle not equal to zero, this is recognized by the software and the endoscope is accordingly displayed as the navigated instrument. Furthermore, a layout adaptation is performed. If the endoscope was recognized as the navigated instrument, in particular the signal of the proximal coil is used to measure the position of the endoscope in the working field and thus to display the position in relation to the image data set of the patient. If the orientation of the two sensors is not equal to the accurately defined sensor unit introduced into the flushing channel of the endoscope, a rotationally-symmetrical instrument (hollow needle) is output by the navigation unit together with the corresponding layout representation. The signal of the distal wire sensor is used to determine the instrument location in the working field and displayed accordingly in the image data set of the patient.

The use of the sensors according to the invention preferably takes place in an endoscope device, which also comprises the sensor unit in addition to an endoscope. It accordingly comprises a sensor unit having at least two sensor coils arranged having a fixed finite spacing in relation to one another in the longitudinal direction, which are oriented at a finite angle in the endoscope in relation to one another.

Because the two sensors are arranged at a finite angle in relation to one another in the endoscope device, because of the different arrangement, the orientation of the endoscope device in the magnetic field of a control and processing electronics unit and thus also in space can be precisely determined.

In one preferred design, it is provided in this case that the first sensor is oriented parallel to the center axis or the main extension direction of the cavity and the second sensor is oriented at a finite angle in relation to the center axis, wherein in particular the first sensor is arranged in the shaft of the endoscope and the second sensor is arranged in an attachment of the insertion head. Therefore, by way of the sensor signal of the sensors in the applied electromagnetic field, the location thereof can also be determined and, because of the fixed spacing to the distal end of the shaft, the location of the distal end of the shaft in the electromagnetic field and thus in space can be determined.

In one refinement, it is provided that the sensor unit bearing the two sensors extends through a cavity of the endoscope device, wherein in particular the sensor unit is connected in an axially fixed manner to an adapter which is attachable to the attachment of the insertion head. In this way, the location of the one sensor, in particular of the—first—distal sensor at the distal end of the shaft is accurately defined in the endoscope device and thus on the basis of the determination of the location of the first—distal—sensor coil by a control and processing electronics unit in the magnetic field, the exact determination of the accurate location of the distal operating location is also possible.

Due to the fixed connection of the sensor unit bearing the sensor coils to a holder separable from the endoscope, furthermore, after positioning, the sensor unit bearing the sensor is removed, and the cavity occupied thereby for the positioning can be released for other usage purposes. Furthermore, the sensor unit is thus separable from the actual endoscope and can be used in another way. This also enables simpler sterilization.

This also applies correspondingly, as described above, for other surgical instruments, such as guide rods, penetration needles, or the like, wherein the above is applicable in the same manner.

Further features and advantages of the invention result from the claims and from the following description, in which exemplary embodiments of the invention are explained in detail with reference to the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5b is a sectional distal end view of the guide rod of FIGS. 5, 5a;

FIG. 6b is a sectional view through a complete Jamshidi needle, in which the sensors of the sensor unit (this without adapter part) are indicated;

DESCRIPTION OF PREFERRED EMBODIMENTS

Figure 1:
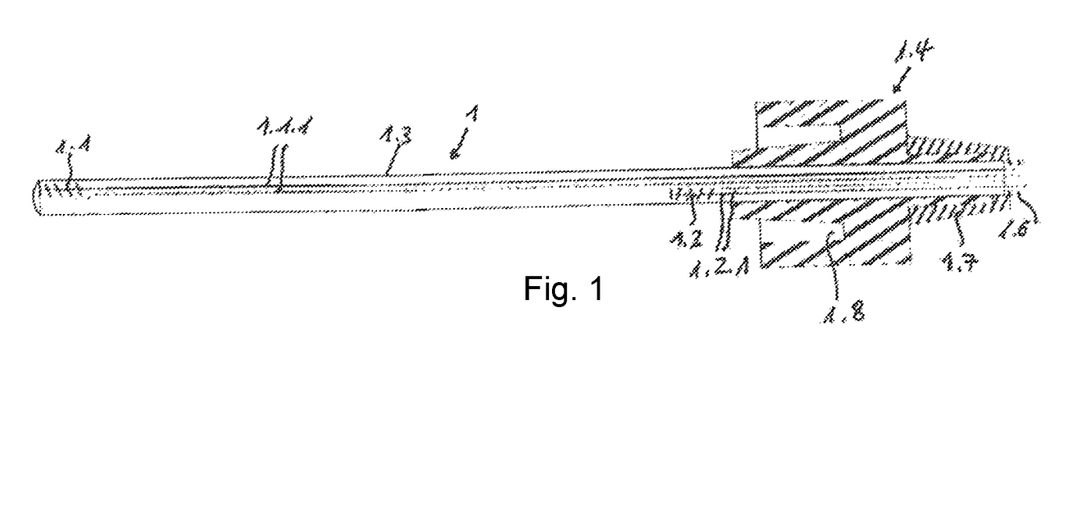
FIG. 1 is a sectional view showing a sensor unit according to the invention in the elongated state.

Referring to the drawings, FIG. 1 shows a sensor unit 1 according to the invention as part of a detection system according to the invention. It comprises two sensors 1.1, 1.2, which are arranged with fixed longitudinal spacing in relation to one another, are formed as coils, and are thus referred to hereafter. The coils 1.1, 1.2 have a fixed longitudinal spacing. They are housed in a tubing 1.3. Each coil 1.1, 1.2 comprises a proximally attached contact line 1.1.1, 1.2.1. Coils 1.1, 1.2 and contact lines 1.1.1, 1.2.1—each having feed and return conductor—consist of conductive metal, preferably copper. They are electrically insulated from one another, for example, by coating using insulating lacquer. A male Luer adapter part 1.4 is provided proximal of the proximal coil 1.2. This adapter part comprises a cylindrical ring space 1.8 distally, using which it can be attached in a defined manner to a cylindrical jacket of an inlet of a corresponding surgical instrument or its associated adapter part. Proximally thereof, a connecting cable 1.5 extends, in which the contact lines 1.1.1, 1.2.1 of the coils 1.1, 1.2 are led up to a connecting plug (not shown) for connection to a navigation unit 3.1. The lines are also jacketed by a jacket 1.6 here.

A buckling safeguard 1.7 is provided directly proximal of the Luer adapter part 1.4 to prevent buckling of the cable 1.5.

Protective tubing 1.3, Luer adapter part 1.4, buckling safeguard 1.7, and jacket 1.6 preferably consist of sterilized plastic, in particular biocompatible plastic, specifically in particular tubing 1.3 of polyether, Luer adapter part of nylon, and buckling safeguard 1.7 and jacket 1.6 of silicone.

If the coils 1.1, 1.2 are moved into an inhomogeneous electromagnetic field, as is generated by the control and processing electronics unit 3 via a field generator 2.1, the location of the coils and the orientation of the coil perpendicular to the axis thereof may thus be determined reliably by means of the coils, while a rotation around the coil axis itself cannot be recognized. Such a sensor is referred to as a 5-DOF sensor (DOF=degree of freedom).

Since in the case of a hollow needle, the distal end of which is located at the operation location, the knowledge of the location of the distal end of the hollow needle (and thus also of a separately introduced working instrument) in space and the orientation of the hollow needle (and of the working instrument, but not of the rotation of the hollow needle and of the working instrument around the axis thereof) is important, such a 5-DOF sensor is sufficient for the determination of the orientation of the distal end of the hollow needle and of the working tool and can be determined by a sensor, which is introduced up to the distal end of the hollow needle, in the inhomogeneous field.

Figure 2:
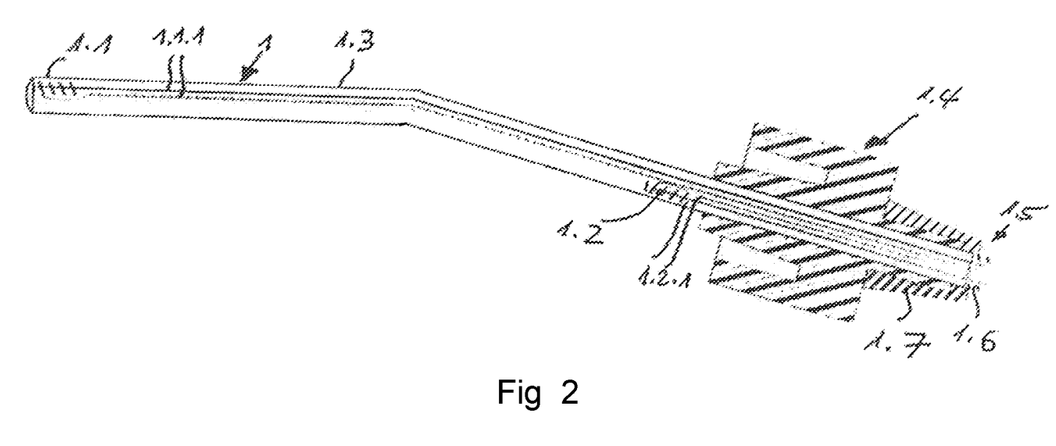
FIG. 2 is a sectional view showing the sensor unit according to the invention of FIG. 1 in the unwound state.

According to FIG. 2, by way of a second corresponding coil 1.2, which is arranged having known longitudinal spacing from the coil 1.1, in the case of a non-rotationally-symmetrical device, such as an endoscope, upon orientation of the two coils 1.1, 1.2 at a finite angle in relation to one another, the orientation of the instrument in question, such as an endoscope, can also be determined, as is the case in the illustration of FIG. 2.

The combination of the two coils 1.1, 1.2 and thus the sensor unit 1 thus overall forms a 6-DOF sensor.

Figure 3:
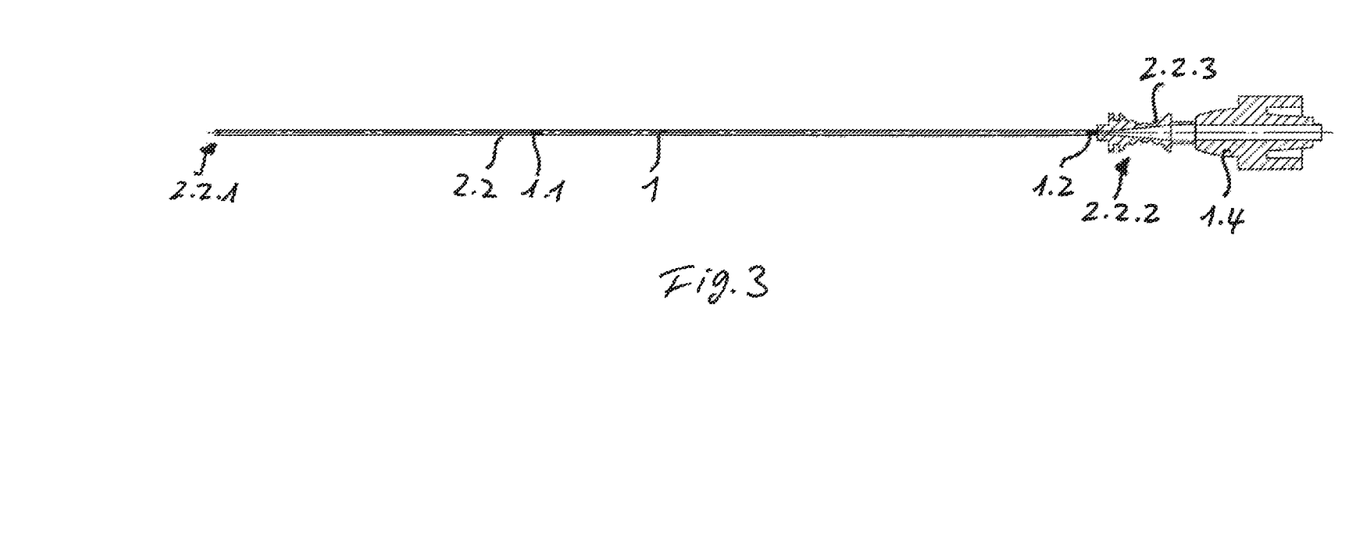
FIG. 3 is a sectional view showing a hollow needle having an elongated sensor unit having aligned sensors.
Figure 4:
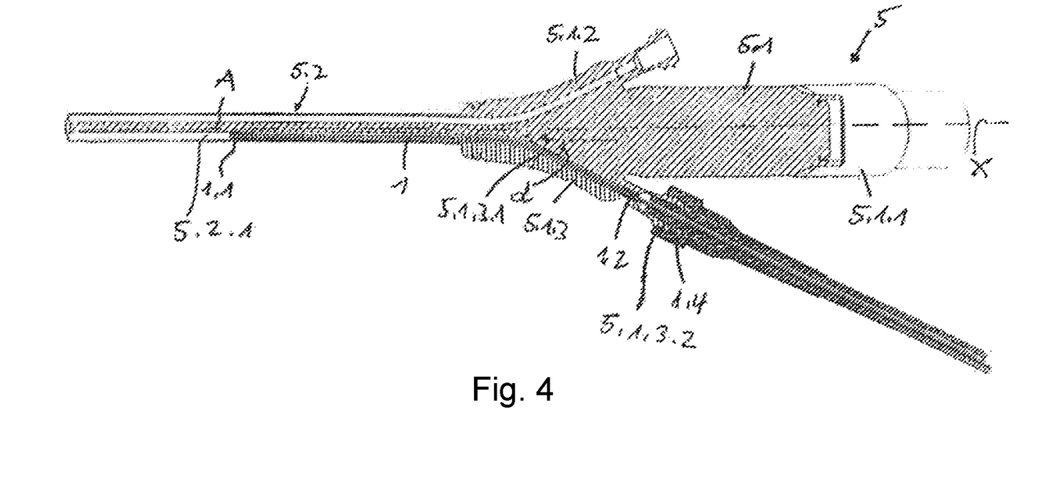
FIG. 4 is a sectional view showing the arrangement of a sensor unit according to the invention in an endoscope to form an endoscope device.

FIG. 3 shows a hollow needle 2.2 having a sensor 1 located therein as part of the detection system according to the invention. The hollow needle is beveled at its distal end 2.2.1 and bears an adapter part 2.2.3 at its proximal end 2.2.2. The sensor unit 1 comprises, as described above, a distal sensor 1.1 and a proximal sensor 1.2. In addition, at the proximal end it covers the adapter part 1.4 which was also already described. The two sensors 1.1 and 1.2 are oriented identically and are arranged aligned with one another, so that the arrangement of the adapter part 1 in a hollow needle 2.2 and therefore this on the basis of this orientation of the two sensors 1.1, 1.2 of the sensor unit 1 can be recognized, as explained in greater detail hereafter with reference to FIG. 7 to FIG. 9. The use of the sensor unit according to the invention in an endoscope is illustrated in FIG. 4 and is explained in greater detail hereafter with reference to this figure.

The endoscope device 5 therein comprises in the illustrated exemplary embodiment a proximal insertion head 5.1 and a shaft 5.2 extending distally therefrom, having at least one oblong cylindrical cavity 5.2.1 extending axially in the shaft 5.2. The insertion head 5.1 has three branches or attachments 5.1.1 to 5.1.3 here, namely an attachment 5.1.1 for connection of a light guide and the optical unit (camera system) and a working channel for the introduction of surgical instruments.

A sensor unit 1 extends in the axially elongated cavity 5.2.1 of the shaft 5.2 through an inlet 5.1.3.1 of the attachment 5.1.3. The sensor unit displays two sensors 1.1 and 1.2 in the form of coils in the above-described manner having spacing in the longitudinal extension thereof. Connecting wires (not shown here) extend from the coils 1.1, 1.2 in the proximal direction up to a respective proximal connecting or contact end of the respective wire, possibly in the formation of a plug for connection of the wires to the control and processing electronics unit 3 of the navigation system 2 (not shown).

The coil 1.1 is located at the distal end of the sensor unit 1 and thus inside the shaft 5.2 of the endoscope 5 extending axially-parallel to the center axis X and is therefore also oriented parallel to the center axis X. The coil 1.2 arranged with spacing in relation to the coil 1.1 on the sensor unit 1 is located in the attachment 5.1.3 of the insertion head 5.1 extending at a finite angle in relation to the center axis X, in that the lumen section of the cavity 5.1.3.1 also extends at a finite angle in relation to the center axis X; the orientation or extension of the coil 1.2 in the attachment 5.1.3 also encloses a finite angle in relation to the center axis X. The two coils 1.1, 1.2 are therefore not parallel to one another, but rather are oriented at a finite angle in relation to one another.

In the case of an externally applied inhomogeneous electromagnetic field—as by way of the field generator 2.1—in which the coils 1.1, 1.2 are located, these coils therefore perceive the field differently and transmit different signals to the control and processing electronics unit 3. Due to this different orientation of the coils 1.1, 1.2, the complete placement and orientation of the endoscope device in the electromagnetic field and thus in space is exactly determined.

The sensor unit 1 comprises, as already stated above, a fixedly arranged Luer adapter part 1.4. This is connectable—connected here—to a complementary Luer adapter part 1.4, 5.1.3.2 on the attachment 5.1.3 of the endoscope 5, which both together form a Luer adapter 1.4, 5.1.3.2. The attachment 5.1.3 and the sensor unit 1 can thus be fixedly connected to one another like a bayonet by the Luer adapter in a way known per se. The location of the adapter part 1.4 in relation to the attachment 5.1.3 and also in relation to the head 5.1 and the shaft 5.2 of the endoscope device 5 is thus defined in the fastened state. Since the sensor unit 1, as stated, is provided axially fixed with the holder, the longitudinal position of the coils 1.1, 1.2 and in particular of the distal coil 1.1 in the shaft 5.2 and thus of the endoscope device 5 is also established and therefore also the spacing, in particular the axial spacing of the coil 1.1 to the distal end 5.1.2 of the shaft 5.2. Therefore, by way of the sensor signal of the coil 1.1 in the applied electromagnetic field, its location and, because of the fixed spacing to the distal end 5.1.2 of the shaft 5.2, the location of the distal end 5.2.1 of the shaft 5.2 in the electromagnetic field and thus in space can be determined.

Figure 5:
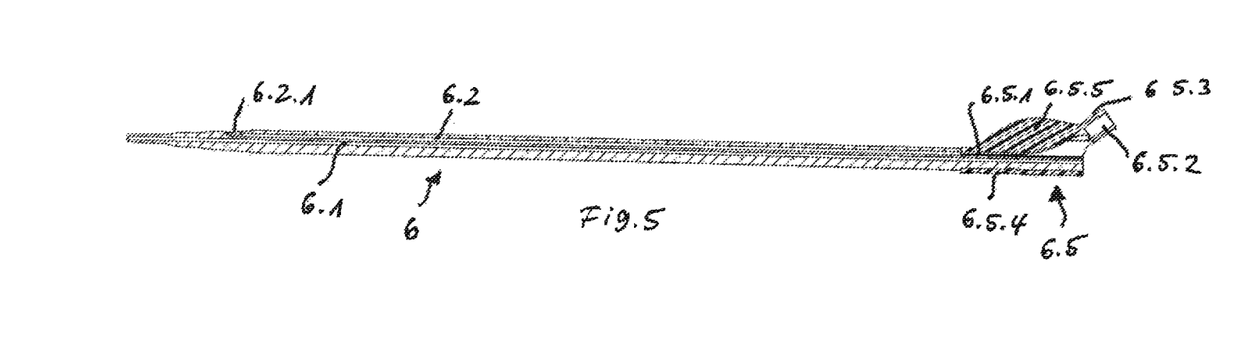
FIG. 5 is a sectional view showing a longitudinal section of a double cannulated guide rod having attached adapter for accommodating a sensor unit of FIGS. 1, 2.
Figure 5A:
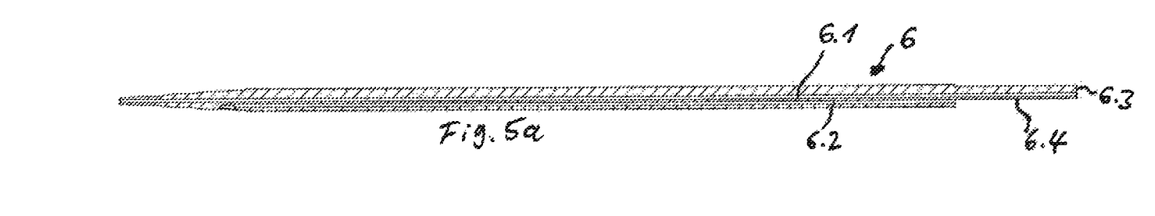
FIG. 5a is a longitudinal sectional view showing the guide rod of FIG. 5 without sensor unit.
Figure 5B:
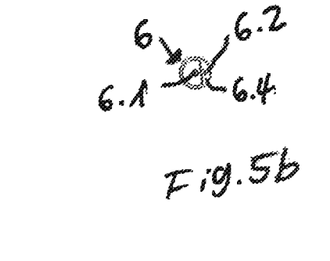
Figure 5C:
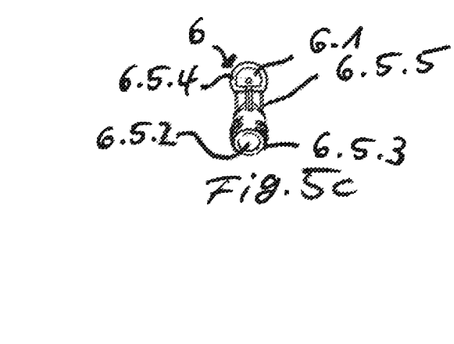
FIG. 5c is a sectional proximal end view of the guide rod of FIG. 5 having attached adapter.

FIG. 5 shows a double cannulated guide rod 6 in longitudinal section having a central oblong cylindrical first cavity 6.1 extending longitudinally through the entire guide rod and a second cylindrical cavity 6.2 extending in parallel thereto over the largest part of the length of the guide rod 6. This cavity opens distally into a lateral opening 6.2.1. The cavity 6.2 also opens proximally with spacing in relation to the proximal end face 6.3 of the guide rod 6, while the cavity 6.1 extends up to the proximal end 6.3. In the proximal region, the guide rod 6 is tapered adjacent to the cavity 6.1 and is provided with an axially-parallel flattening 6.4.

An adapter 6.5, which comprises a cavity 6.5.1 extending the cavity 6.2 in an aligned manner, which in turn ends in an entry region 6.5.2 of the adapter 6.5, is attachable to the proximal end of the guide rod 6. The entry region 6.5.2 has a finite angle in relation to the axial extension of the cavity 6.2, preferably an angle of 35° in relation to the longitudinal axis of the guide rod or the extension direction of the cavity 6.2.

A connecting plate 6.5.5 is provided for stabilizing the adapter 6.5 in the angle between its plug part 6.5.4 and the entry region 6.5.2. The adapter 6.5 is formed in one piece and preferably consists of plastic.

A sensor unit according to FIGS. 1, 2 is inserted through the entry region 6.5.2 up into the cavity 6.2, wherein the distal sensor 1.1 of the sensor unit 1 is located in the distal region of the cavity 6.2 and the sensor 1.2, when the adapter 1.4 is fully plugged on, is located with its distal ring space 1.8 in the form of a cylindrical jacket on the cylindrical jacket wall 6.5.3 of the adapter 6.5 in the region of the angled entry region 6.5.2.

The different orientations of the two sensors 1.1, 1.2 of the sensor unit 1 inserted into the guide rod 6 and in particular the precise angle of the sensors 1.1, 1.2 in relation to one another can be detected by an analysis unit and the display on the display screen of a control unit can be selected and/or adapted accordingly thereto, as is described in detail hereafter in the text both for a hollow needle and also for an endoscope.

Figure 6:
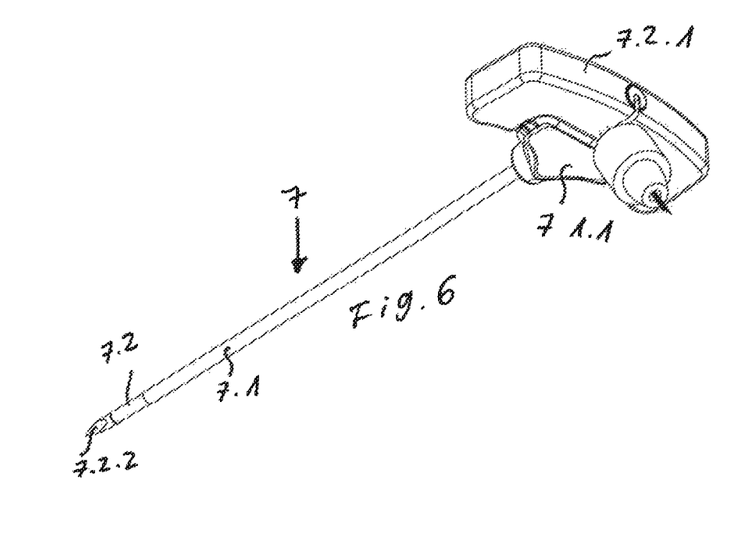
FIG. 6 is a perspective view showing a trephine needle according to Jamshidi.

A trephine needle 7 according to Jamshidi, as shown in FIG. 6, is provided as a further surgical instrument detectable in the scope of the subject matter of the invention and in particular of the detection system. Such a trephine needle 7 is formed in two parts. It comprises, on the one hand, a cannula 7.1 and, on the other hand, a stylet 7.2, which are respectively provided with a handle part 7.1.1 and 7.2.1. The stylet 7.2 protrudes beyond the cannula 7.1 and comprises a pointed distal end 7.2.2, which is to be formed conically or as a trocar. The stylet is formed solid in typical trephine needles 7 of this type.

Figure 6A:
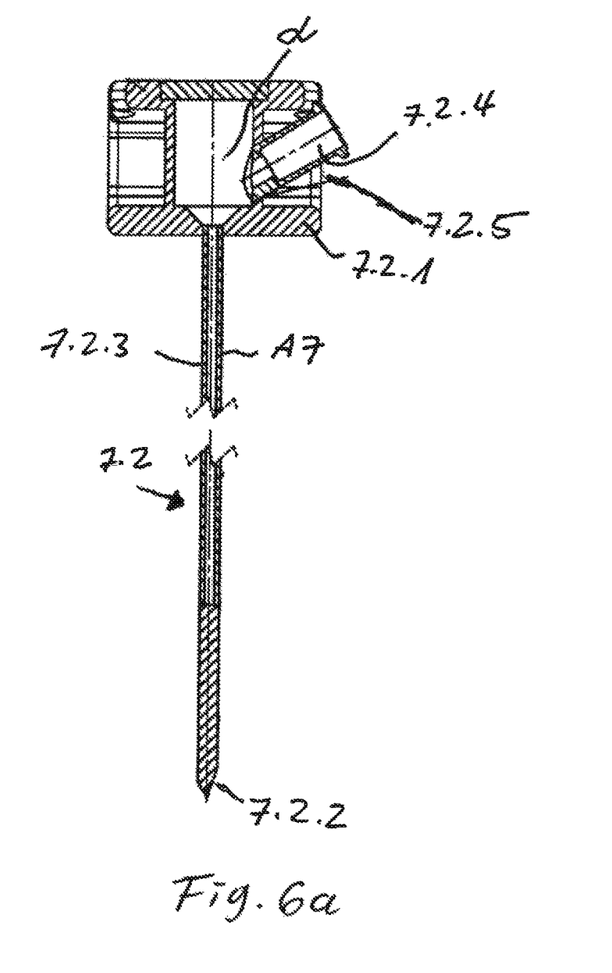
FIG. 6a is a longitudinal sectional view through a trephine needle according to Jamshidi.

The stylet 7.2 according to the invention comprises an axial oblong cylindrical cavity 7.2.3, as is recognizable in the longitudinal section of the stylet 7.2 of FIG. 6*a*. It extends from the proximal adapter part 7.2.1 of the stylet 7.2.1 through the stylet 7.2 and ends with a spacing to the distal tip 7.2.2. The adapter part 7.2.1 in turn comprises an entry region 7.2.4 having an essentially cylindrical jacket wall 7.2.5, which is oriented at a finite angle in relation to the extension direction of the stylet 7.2 or its axis A7. The relative angle α of the entry region 7.2.4 in relation to the axis A7 of the stylet deviates from the relative angles of other surgical instruments usable in the scope of the detector system according to the invention, specifically by at least 5°, and is 65° in the illustrated exemplary embodiment.

A sensor unit 1 of FIGS. 1, 2 is also inserted through the entry region 7.2.4 of the stylet 7.2 of the trephine needle 7 up into the axial cavity 7.2.3 and the adapter part 1.4 of the sensor unit 1 is positioned having its cylindrical ring space 1.8 on the jacket 7.2.5 of the entry region 7.2.4 in such a way that the sensor 1 comes to rest in the distal end region of the axial cavity 7.2.3 of the stylet 7.2, but the sensor 1.2 comes to rest in the inlet 7.2.5 oriented at the mentioned finite angle in relation thereto.

In such a way, the relative position of the sensors 1.1 and 1.2 in an electromagnetic field and in particular the accurate angle orientation can again be determined by the analysis unit and thus the trephine needle 7 according to Jamshidi can be identified as the surgical instrument and the display on the monitor of the processing electronics unit can be displayed accordingly, as is described hereafter, as already stated, for an—elongated—hollow needle and an endoscope. The statements therein also relate in a corresponding manner to the above-described guide rod and also to the trephine needle described here according to Jamshidi.

A detection system according to the invention is formed in particular by the sensor unit 1, at least two of the instruments 2.2, 5, 6, 7, and an analysis unit 3.1.3, which is described hereafter in the scope of a comprising control and processing electronics unit 3.

Figure 7:
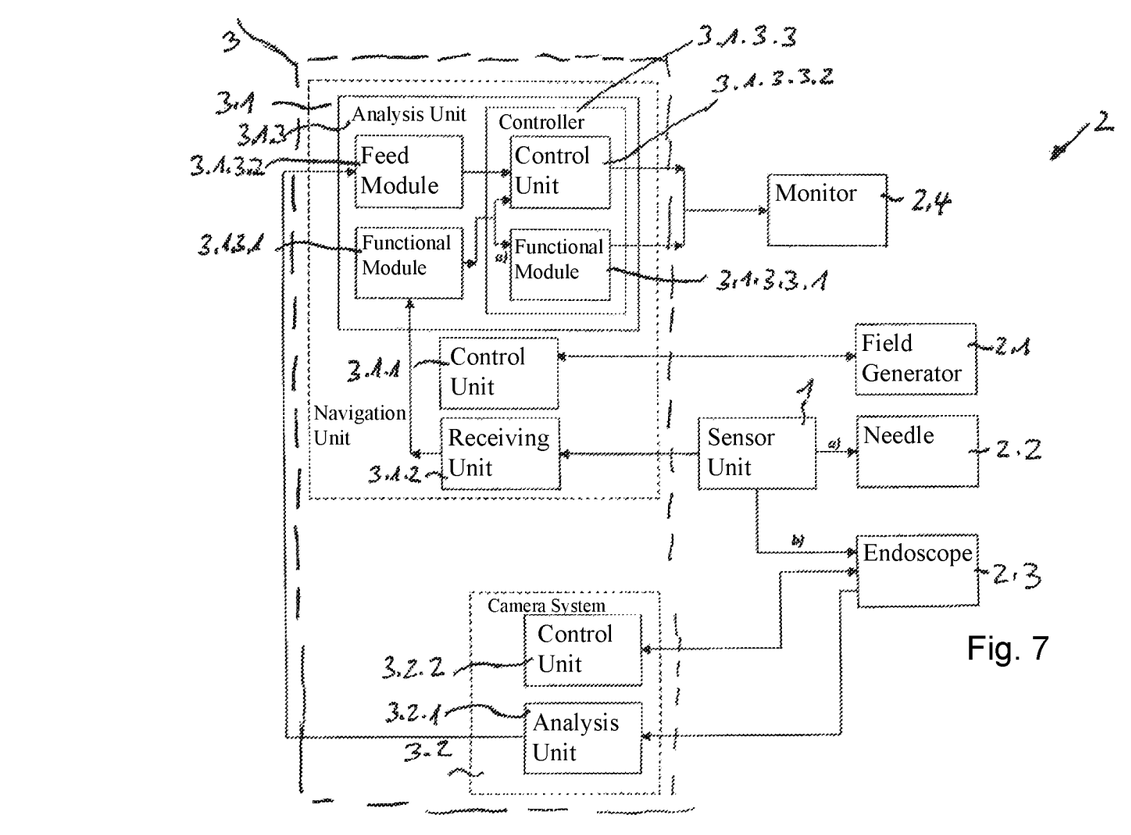
FIG. 7 is a block diagram of the navigation system according to the invention.

FIG. 7 shows a schematic representation like a block diagram of an intraoperative navigation system 2 according to the invention and its essential components. Parts of the navigation system 2 are the sensor unit 1, the control and processing electronics unit 3, the field generator 2.1, at least one rotationally-symmetrical instrument 2.2, such as a hollow needle 2.2, and at least one endoscope 2.3.

The control and processing electronics unit 3 comprises a navigation unit 3.1 and a camera system 3.2 for the endoscope 2.3, as illustrated in FIG. 7.

The navigation unit 3.1 firstly comprises a control unit 3.1.1 for controlling the field generator 2.1. Furthermore, it comprises a receiving unit 3.1.2 connected to the sensor unit 1 for receiving signals S1, S2 of the sensor unit and for the further processing thereof The sensor signals thus received and adapted are further processed by an analysis unit 3.1.3, which can be implemented by software modules. The analysis unit 3.1.3 firstly comprises a functional module 3.1.3.3.1 for instrument recognition, i.e., whether a rotationally-symmetrical instrument 2.2, such as a hollow needle, or a non-rotationally-symmetrical instrument, such as an endoscope 2.3, are attached.

Figure 9:
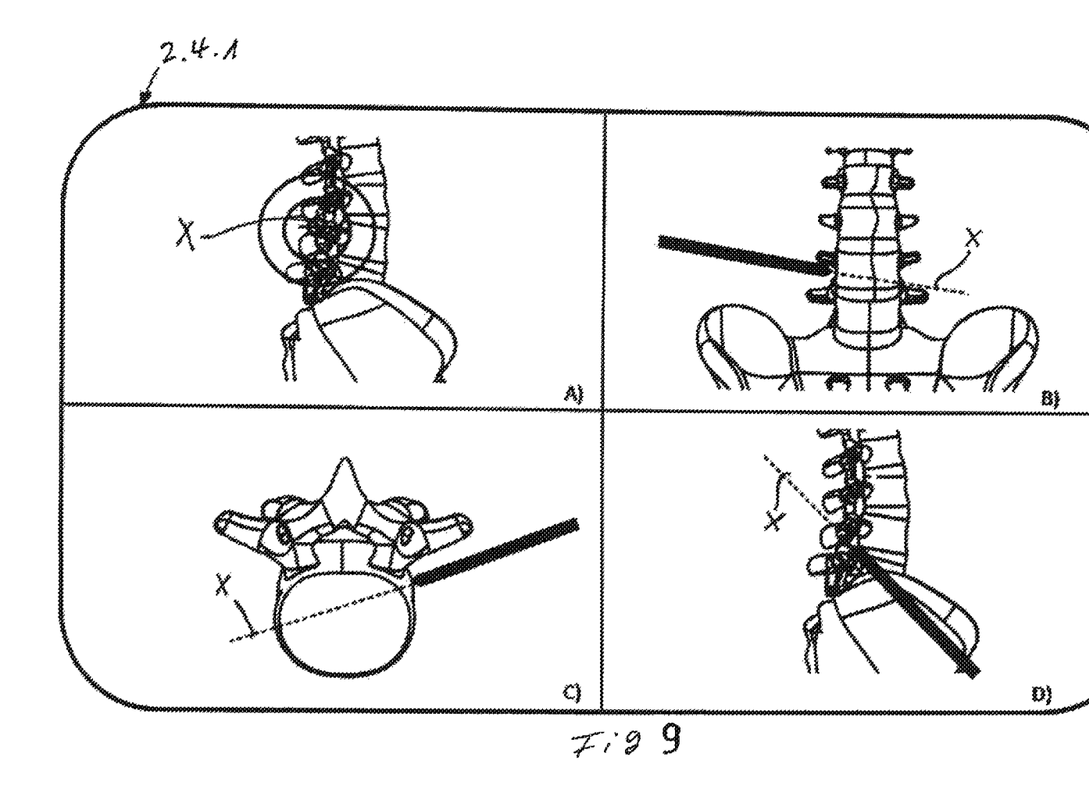
FIG. 9 is a representation, automatically generated by means of the navigation system according to the invention on the basis of the orientation of the sensor unit, of a surgical instrument in overlay with the representation of spinal column regions of a patient in the case of a hollow needle.
Figure 10:
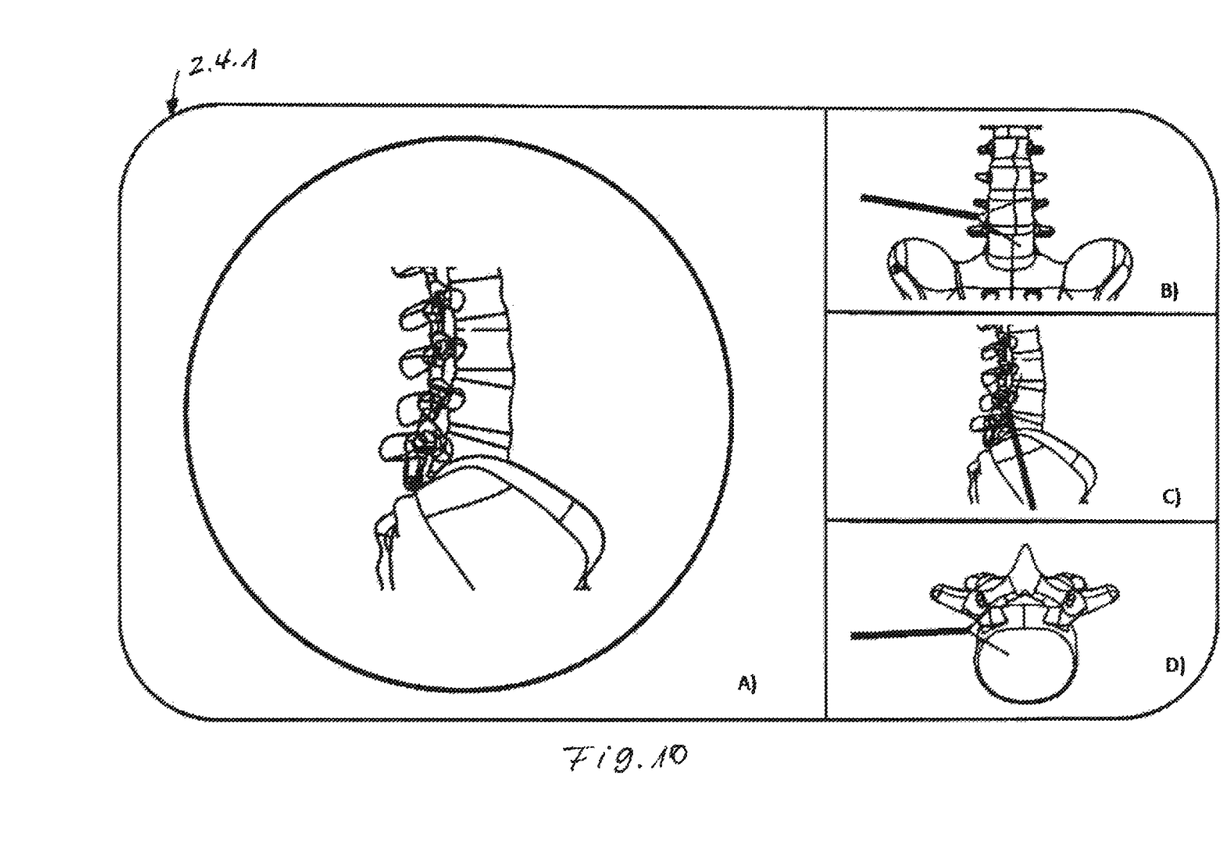
FIG. 10 is a representation, automatically generated by means of the navigation system according to the invention on the basis of the orientation of the sensor unit, of a surgical instrument in overlay with the representation of spinal column regions of a patient in the case of an endoscope.

The functional module 3.1.3.3.1 is in turn connected to a layout controller 3.1.3.3, by means of which the layout of the representation on the monitor is controlled, specifically via the functional module 3.1.3.3.1 in the case of a rotationally-symmetrical instrument 2.2 in accordance with FIG. 9 and via the functional module 3.1.3.3.1 in the case of an endoscope 2.3 in accordance with FIG. 10 using the endoscope image.

The analysis unit 3.1.3 furthermore comprises a feed module 3.1.3.2 for feeding the video signal of the endoscope 2.3 into the representation of the monitor image of FIG. 10 effectuated by the functional module 3.1.3.1.

The video signal of the endoscope 2.3 is supplied to the navigation unit 3.1 via a camera system 3.2 of the endoscope 2.3, which comprises an analysis unit 3.1.3 for processing the image of the endoscope 2.3, on the one hand, and a control unit 3.1.1 for controlling the camera of the endoscope, on the other hand.

Figure 8:
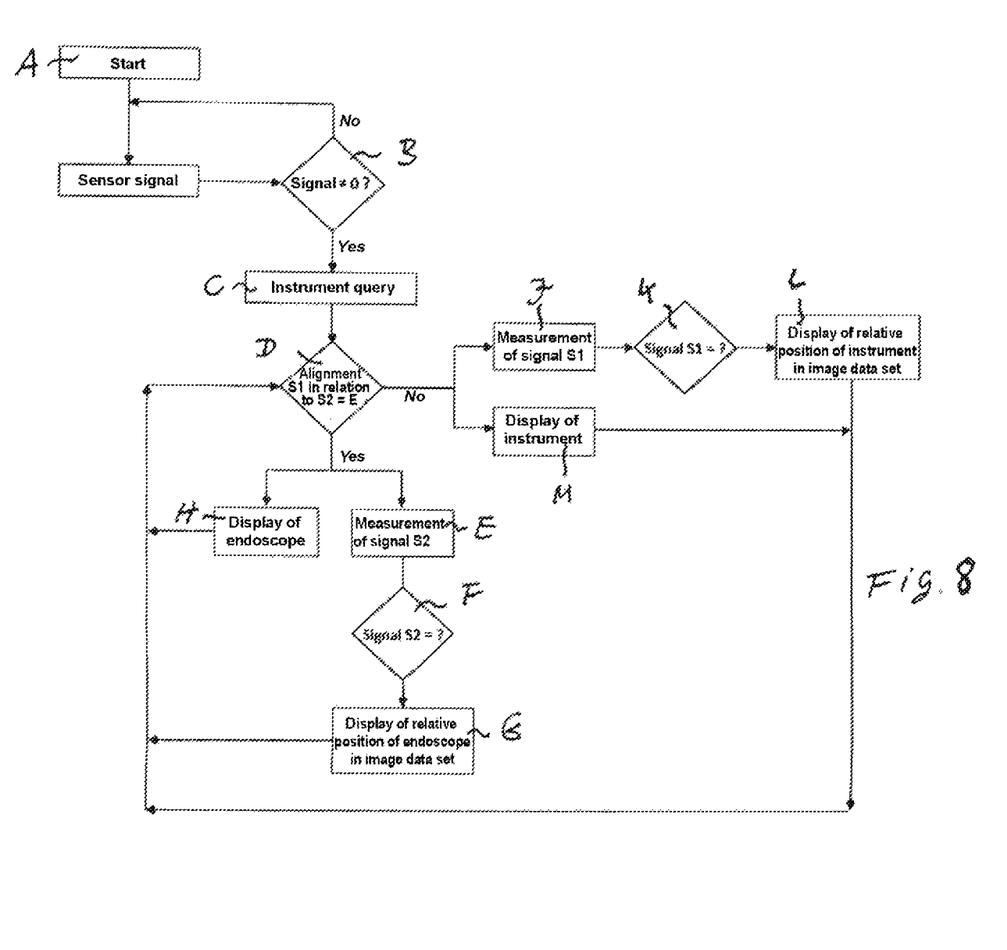
FIG. 8 is a flow chart of the method according to the invention.

The working sequence of the navigation system according to the invention is as follows according to FIG. 8:

After starting the navigation unit 3.1, the signals of the sensors are requested. As soon as the user moves the sensor unit 1 into the working field of the field generator 2.1, a signal can be recognized and measured. If, according to sequence B, the sensor signal is not equal to the value zero and corresponds to the sensor unit 1, an instrument query C takes place. For this purpose, the orientation of the two sensor coils (step D) is analyzed. If the two coils 1.1, 1.2 are at a finite relative angle not equal to zero in relation to one another in accordance with the geometry of the flushing channel in this case (distance and angle), this is recognized by the software and the endoscope 2.3 is accordingly displayed as the navigated instrument. Furthermore, a layout adaptation is performed according to FIG. 10. If the endoscope 2.3 was recognized as the navigated instrument, a signal of the proximal sensor coil 1.2 is used to measure the position of the endoscope in the working field (step E) and to display the position in relation to the 3D image data set on the basis of the measurement F (step G). Furthermore, as already described, the endoscope image is introduced in the monitor. In particular, on the basis of the known location of the coil 1.2 in the endoscope, the position of the distal end of the endoscope in space can be concluded and this can be represented in the image of the spinal column region, as shown in FIG. 10.

If in step D, an orientation of the two sensor coils 1.1, 1.2 is determined not equal to the precisely defined location in accordance with the one flushing channel of the endoscope in relation to its main axis of in general 25°, a rotationally-symmetrical instrument (needle) is recognized and output together with the corresponding layout representation by the navigation system (step H). The sensor coil 1.1 is used to determine the instrument location in the working field (step J) and displayed according to the measured location (step K) in the 3D image data set (step L).

If the navigation system recognizes, because of the axial orientation of the two coils 1.1, 1.2 in the inhomogeneous field, i.e., an orientation at a relative angle which does not correspond to the arrangement of the averted connection of an endoscope in relation to its main axis, generally of 25°, in particular is less than this angle, that a hollow needle 2.2 is used as a rotationally-symmetrical instrument, a representation is thus automatically displayed to the user on a monitor 2.4, in which the body of the patient, more precisely a spinal column region or parts of the region—the spinal column 4 here—are represented from four views with overlay of the representation of the operation instrument or the hollow needle 2.2, respectively. The representations are based on an image data set of a patient, which is obtained by means of computer tomography (CT) or magnetic resonance tomography (MRT) (because of requirements for the patent form, FIG. 9 and FIG. 10 only show simplified schematic illustrated representations of the colored or grayscale image actually displayed on the monitor 2.4 and also only show the operation instrument or the shaft, respectively, in a black representation and the distal end of the endoscope, which is actually displayed offset in color on the monitor 2.4).

In the monitor image 2.4.1, the region of the spinal column 4 corresponding to a target display of the instrument is illustrated on the top left (A), i.e., in the axial direction of the instrument or the hollow needle 2.2 in the direction of the axis X of the instrument or the hollow needle 2.2, respectively (the further illustrations of FIG. 9 also for this purpose). On the right adjacent thereto (B), a sagittal display is performed, i.e., the representation of a plane the perpendicular of which is oriented sagittally, i.e., from the back towards the rib cage of the patient. The illustration on the bottom left (C) is an axial display, i.e., corresponding to the extension direction of the spinal column. The last illustration on the bottom right (D) shows a coronal display, i.e., from the side.

If the navigation system 2 recognizes an endoscope by way of orientation of the two coils 1.1, 1.2 at a finite angle in accordance with the angle between main axis of the endoscope and proximal branch of in general 25°, in the large image part on the left of the monitor corresponding to FIG. 10, the real image of the camera of the endoscope is thus displayed. The images on the right from top to bottom (B-D) again show the displays described with reference to FIG. 9, specifically B sagittal, C coronal, and D axial here, as a comparison to FIG. 9 also shows.

The navigation system according to the invention directly recognizes, on the basis of the orientation of the two coils of the sensor unit in relation to one another, the type of surgical instrument, the distal end of which is located at the operation location, and the corresponding representation relevant to it is automatically displayed to the operator on the monitor 2.4.

An operator thus accurately recognizes on the basis of the analysis of the sensor signals and an image display on a display screen of the analysis unit the position of the distal end 5.2.1 of the shaft 5.2 and thus also of the endoscope device 5 and thus knows where exactly they are working with their instruments, which they possibly introduce into another lumen of the endoscope device and through it. This applies accordingly in the case of the orientation of the sensor unit 1 in a hollow needle 2.2.

While specific embodiments of the invention have been shown and described in detail to illustrate the application of the principles of the invention, it will be understood that the invention may be embodied otherwise without departing from such principles.

The invention claimed is:

1. A detection system for automatically detecting surgical instruments, the detection system comprising:
   at least two surgical instruments, which each comprise a cavity extending along a longitudinal axis of the instrument and a proximal entry region, the first instrument having a first angle between the longitudinal axis and the entry region of the first instrument, the second instrument having a second angle between the longitudinal axis and the entry region of the second instrument, wherein the first angle and the second angle are different;
   a sensor unit comprising two electromagnetic sensor units, one sensor of each of the electromagnetic sensor units axially extending in the cavity, and a second sensor of each of the two electromagnetic sensor units being arranged in the entry region of each instrument;
   a field generator for generating an electromagnetic field, each of the one sensor and the second sensor being configured to detect the electromagnetic field and to generate an electric signal as output based on detection of the external electromagnetic field; and
   an analysis unit comprising a processor for analyzing signals transmitted by the sensors to the analysis unit in accordance with the location thereof in the field of the field generator, the analysis unit comprising the processor being configured to determine a surgical instrument type of one of the at least two surgical instruments based on the signals transmitted by the one sensor and the second sensor of one of the electromagnetic sensor units.

2. A detection system according to claim 1, wherein:
the at least two surgical instruments comprise at least two of the following instruments: a hollow needle, a guide rod, a penetration needle according to Jamshidi, and an endoscope;
the analysis unit is configured to determine a type difference of the at least two surgical instruments based on the signals.

3. A detection system according to claim 2, wherein the guide rod is double cannulated.

4. A detection system according to claim 1, wherein the at least two surgical instruments comprises at least four different instruments.

5. A detection system according to claim 4, wherein angles of the entry regions in relation to the longitudinal extension of the cavity of two instruments differ by at least 5°.

6. A detection system according to claim 5, wherein the entry regions have angles of 0°, 15°, 25°, 35°, 45°, 55°, 65°, or 75° in relation to the longitudinal extension of the cavity.

7. A detection system according to claim 6, wherein the sensors have a fixed longitudinal spacing in relation to one another.

8. A detection system according to claim 7, wherein the sensors are coils made of electrically conductive wire.

9. A detection system according to claim 8, wherein the coils are comprised of metal.

10. A detection system according to claim 9, wherein the sensor unit comprises a flexible protective tubing jacketing the sensors.

11. A detection system according to claim 10, wherein the protective tubing comprises plastic, which is sterilizable.

12. A detection system according to claim 1, wherein the proximal entry region is comprised of a Luer adapter that comprises an adapter part.

13. A detection system according to claim 1, wherein the sensors comprise an electrical connecting line at a sensors proximal end, for connection to the analysis unit.

14. A detection system according to claim 13, wherein the electrical connecting line is enclosed by a protective tubing made of biocompatible plastic which is sterilizable.

15. A detection system according to claim 13, wherein the electrical connecting line is enclosed by a protective tubing and the protective tubing is enclosed directly proximal of an adapter part of the sensor unit by a buckling safeguard.

16. A detection system according to claim 15, wherein the buckling safeguard is enclosed by biocompatible plastic which is sterilizable.

17. A detection system according to claim 1, wherein the analysis unit is part of a control and processing electronics unit, the analysis unit being further configured to determine a type of another one of the at least two surgical instruments based on the signals transmitted by the one sensor and the second sensor of another one of the electromagnetic sensor units.

18. A detection system according to claim 1, further comprising a monitor.

19. A detection system according to claim 1, wherein the system is configured to represent at least a portion of the at least two instruments, comprised of any combination of hollow needles, a guide rod, which is double cannulated, a penetration needle, and an endoscope, overlaid in an image of a spinal column region of a patient.

20. An interactive navigation device comprising:
a control and processing electronics unit; and
a detection system comprising:
two surgical instruments, which each comprise a cavity extending along a longitudinal axis of the instrument and a proximal entry region, the first instrument having a first angle between the longitudinal axis and the entry region of the first instrument, the second instrument having a second angle between the longitudinal axis and the entry region of the second instrument, wherein the first angle and the second angle are different;
a sensor unit comprising two electromagnetic sensor units, one sensor of each of the two electromagnetic sensor units axially extending in the cavity, and a second sensor of each of the two electromagnetic sensor units being arranged in the entry region of each instrument;
a field generator for generating an electromagnetic field, each of the one sensor and the second sensor being configured to detect the electromagnetic field and to generate an electric signal as output based on detection of the electromagnetic field; and
an analysis unit comprising a processor for analyzing signals transmitted by the sensors to the analysis unit in accordance with the location thereof in the field of the field generator, wherein the control and processing electronics unit comprises a navigation unit, in which the analysis unit is adapted, the analysis unit comprising the processor being configured to determine a surgical instrument type of one of the at least two surgical instruments based on the signals transmitted by the one sensor and the second sensor of one of the electromagnetic sensor units.

* * * * *